United States Patent [19]

Coombs

[11] Patent Number: 4,958,901

[45] Date of Patent: Sep. 25, 1990

[54] METHOD FOR MAKING A MULTI-LUMEN EPIDURAL-SPINAL NEEDLE AND TIP AND STOCK CONFIGURATION FOR THE SAME

[75] Inventor: Dennis W. Coombs, Etna, N.H.

[73] Assignee: Neurodelivery Technology, Inc., Tempe, Ariz.

[21] Appl. No.: 316,037

[22] Filed: Feb. 27, 1989

Related U.S. Application Data

[63] Continuation-in-part of Ser. No. 72,428, Jul. 13, 1987, Pat. No. 4,808,157.

[51] Int. Cl.⁵ .............................................. A61M 3/00
[52] U.S. Cl. ........................................ 604/44; 604/52; 604/158; 604/272; 264/145
[58] Field of Search ...................... 604/43–44, 604/51–53, 158–169, 272–274; 425/DIG. 59; 264/145, 285; 248/68.1

[56] References Cited

U.S. PATENT DOCUMENTS

| | | | |
|---|---|---|---|
| 31,873 | 4/1985 | Howes | 604/43 |
| 2,542,442 | 2/1951 | Weber | 248/68.1 |
| 3,788,119 | 1/1974 | Arrigo | 604/274 |
| 3,788,320 | 1/1974 | Dye | 604/272 |
| 3,804,097 | 4/1974 | Rudie | 128/350 R |
| 4,134,402 | 1/1979 | Mahurkar | 604/272 |
| 4,518,383 | 5/1985 | Evans | 604/272 |
| 4,645,491 | 2/1987 | Evans | 604/158 |
| 4,737,146 | 4/1988 | Amaki et al. | 604/43 |
| 4,808,157 | 2/1989 | Coombs | 604/52 |
| 4,842,585 | 6/1989 | Witt | 604/158 |

FOREIGN PATENT DOCUMENTS

| | | | |
|---|---|---|---|
| 834211 | 10/1975 | Belgium | 604/44 |
| 624618 | 9/1978 | U.S.S.R. | 604/160 |
| 8606968 | 12/1986 | World Int. Prop. O. | 604/44 |

OTHER PUBLICATIONS

Combined Spinal–Epidural Needle, Joseph Eldor M.D. Regional Anesthesia, vol. 15, No. 15, Jan.–Mar. 1988, Supplement, p. 89, Abstracts Prescribed at American Society of Regional Anesthesia Annual Meeting, Mar. 17–20, 1988.

Combined Spinal–Epidural Needle (CSEN), Joseph Eldor M.D., Canadian Journal of Anesthesia, vol. 35, No. 5, Sept. 1988, pp. 537–539.

Primary Examiner—Stephen C. Pellegrino
Assistant Examiner—Michael Rafa
Attorney, Agent, or Firm—Michael J. Weins

[57] ABSTRACT

The present invention discloses a method for producing a multi-lumen needle suitable for administrating spinal anesthesia. The method will provide a needle that will allow the simultaneous administration of spinal and epidural anesthetic from a single site. A preferred needle made by this method can optionally be made with a stock configuration which has means for holding a catheter during the insertion of a spinal needle and is configured so as to provide gripping sites to assist in positioning the needle. The preferred needle of the present invention has a lumen which can serve as a spinal introducer. The introducer lumen sheaths the spinal needle until the spinal needle is in the epidural space. This assures that the spinal needle will not be bent or fractured in use by impingement with bone or hard tissue.

18 Claims, 4 Drawing Sheets

METHOD FOR MAKING A MULTI-LUMEN EPIDURAL-SPINAL NEEDLE AND TIP AND STOCK CONFIGURATION FOR THE SAME

FIELD OF INVENTION

The present invention is a continuation in part of U.S. patent application No. 07/072,428, filed 07/13/87 now U.S. Pat. No. 4,808,157 issued 02/28/89 herein incorporated by reference. The present invention is directed to a method for making an epidural-spinal needle and an improved tip and stock configuration for the same.

BACKGROUND

Punctures of the spinal area are required in conjunction with a variety of medical and surgical procedures. Frequently medication, and in particular, epidural and spinal anesthetics must be introduced through a needle or a catheter. It may be desirable to both introduce medication in the vicinity of the puncture through a spinal needle and to introduce medication through a catheter to a location remote from the puncture in the epidural or spinal spaces.

Using prior art techniques, multiple punctures would have to be made for simultaneous introduction of an epidural catheter and a spinal needle, or for the introduction of two epidural and/or spinal catheters. Multiple spinal punctures have greater risk than a single puncture because of the increased trauma from additional punctures and because the time required to perform the procedure must be extended.

Spinal anesthesia frequently requires the initial administration of small quantities of an anesthetic agent into the subarachiod space. Since spinal anesthesia may be effective for only short periods of time, an adjunctive epidural anesthetic technique that can be continuous may be required for longer surgical procedures. Alternatively, either continuous epidural or spinal techniques must be utilized. The epidural technique yields a less dense local anesthetic block, while the spinal technique can lead to equally undesirable consequences including post spinal headache. Significant advantages could be obtained if the epidural and spinal procedures could be combined.

A procedure using conventional prior art single lumen needles to administer the spinal and epidural anesthetic requires the procedures either be performed at separate sites, or the two procedures be separated by a time interval. It would be advantageous and would reduce trauma if both procedures could be carried out nearly simultaneously at the same site utilizing small gauge spinal needles. If both procedures were carried out simultaneously utilizing one puncture the length of the procedure, and the discomfort to the patient would be reduced.

One option for using a single needle is to use a needle to locate the epidural space and then to insert a spinal needle through the needle to such an extent that the spinal needle penetrates the dura. An anesthetic agent can then be administered through the spinal needle. The spinal needle can then be withdrawn, leaving the needle in position for use in introduction of an epidural catheter in the usual way. This technique may have a significant risk in that the epidural catheter will pass into the space through the perforation and be undetected. Also the immediate epidural catheterization is not assured.

If a single needle is not used for the administration of the spinal and epidural anesthetic, but rather multiple needles are used, multiple punctures must be made in separate locations. One puncture is used for the insertion of, and to guide the spinal needle while the other puncture is used for the introduction of a catheter or for the introduction of a second needle.

If combined spinal and epidural anesthesia is to be used, the time to complete the epidural must be minimized once the spinal anesthetic is injected since a dangerous situation may occur such as serious drops in blood pressure and/or pulse rate once the spinal anesthetic has been administered. This dangerous situation may arise during performance of the epidural catheterization since using prior art techniques epidural catheterization must be performed subsequent to the spinal anesthetic injection unless multiple needles and multiple punctures are used.

The above mentioned problems have been largely over come by an epidural-spinal needle which is disclosed and claimed in U.S. patent application No. 07/072,428. The epidural-spinal needle is a dual lumen needle having lumen of different gauges. The larger lumen is sized to pass a catheter and configured to direct a catheter into and along the epidural space. The smaller lumen serves as an introducer for a fine gauge spinal needle. The purpose of the introducer is to assure that the fine gauge spinal needle passes into the epidural space without being bent or fractured by bone and tissue matter which it must pass through before entering the epidural space.

The epidural-spinal needle serves to locate and cannulate the epidural space, introduce a spinal needle into the epidural space, introduce a spinal or epidural catheter, or the introduction of multiple catheters through a single puncture resolving many of the problems of the earlier needles. It will allow for the simultaneous introduction of one or more needles, a needle and a catheter, or multiple catheters through a single skin puncture. Thus the epidural-spinal needle has advantages with respect to the prior art by reducing trauma, reducing procedure time, and providing the practitioner with a greater flexibility regarding the positioning of the catheters and needles for a specific procedure since the needle of the present invention can function as an introducer.

The present invention provides a method for making the epidural-spinal needle of the U.S. application No. 07/072,428 as well as an improved tip and stock configuration for an epidural-spinal needle.

The tip configuration of the present application further reduces the trauma of insertion of an epidural-spinal needle, guides the spinal needle into the epidural space without obstruction from bone or tissue, and directs a spinal needle into the dura at an angle. Having a skewed path through the dura wall assists the sealing of the wall when the needle is removed and in this manner further reduces the chance of dural headaches.

The improved stock provides reference surfaces for aligning the catheter and spinal needle to aid in the insertion of the catheter and spinal needle; additional grips for holding and inserting the spinal needle; and means for holding catheters during insertion of the spinal needle.

SUMMARY OF THE INVENTION

It is an object of the present invention to provide a method for making an epidural-spinal needle.

It is another object of the invention to provide a stock for an epidural-spinal needle contoured to provide multiple grips for inserting and positioning the epidural-spinal needle.

It is a further object of the invention to provide a stock with means for holding a previously inserted epidural catheter during insertion of a spinal needle through the epidural-spinal needle.

It is still another object of the present invention to provide reference surfaces which aid in aligning and inserting the catheter and the spinal needle.

It is a further object of the invention to provide an introducer for spinal needles that directs a spinal needle through the dura wall on a skewed path thereby limiting seepage of fluids between the dura and epidural space when a spinal needle is withdrawn from the dura.

These and other objects of the present invention will become apparent from the following figures and description.

In making an epidural-spinal needle the appropriate gauge needle tubing should be selected based on its intended use. The epidural tubing should be chosen such that its larger lumen, the epidural lumen, passes the catheter for which it will be used. Generally, the epidural lumen tubing of the epidural-spinal needle should have a gauge size less than 14 gauge and preferably between approximately 16 and 20 gauge and preferably about 18 gauge.

When the epidural-spinal needle serves as an introducer for very small spinal needles of 25 to 32 gauge, the size of the smaller or introducer tubing should be between 20 and 24 gauge and preferable 21 or 22 gauge.

Such a range of gauges will accommodate a spinal needle of between 25 and 32 gauge. The small spinal needle can in turn be used for a spinal puncture or microcatheters can be inserted intrathecally through the small gauge spinal needle once the dura has been punctured.

In fabricating an epidural-spinal needle, the needle tubing for the spinal lumen and the introducer lumen are aligned such that the axes of the lumina are parallel and the needle tubing bounding the lumina have a line of contact. With the needle tubing so positioned a needle blank is formed by bonding the tubing for the epidural lumen to the tubing for the introducer lumen. Starting at the first end which becomes the tip end, the tubing for the lumina are bonded along the line of contact for a length sufficient to form a tip region, a needle body, and an unbonded region. Preferably this length will be between about 3.7 and 5.7 inches for adult patients; the tip and needle body for adults being between about 2.5 and 4.5 inches. The direction of insertion for the resulting needle will be parallel to the axes of the lumina and the line of contact in the body of the needle. The unbonded region of the needle blank forms the extensions of the epidural lumen and the introducer lumen.

The tip region of the needle blank body is bent in the plane defined by the lumen axes. The axis of the epidural lumen after bending is convex with respect to the introducer lumen in the tip region. The minimum radius of curvature of the needle tubing in the tip region is preferably between about ½ and ⅜ inches.

The epidural tubing is cut in the tip region providing a first tip piercing surface inclined with respect to the insertion direction of the needle by an angle sigma. Preferably sigma is not more than about 30 degrees.

The piercing surface for the epidural lumen is cut such that the piercing surface intersects the line of contact at a first piercing point at a distance normal to the line of contact of the lumina for the body of the needle that is greater than the radius of the epidural lumen tubing. It is further preferred that the first piercing surface does not extend beyond the crown by more than about the thickness of the epidural tubing. Where the crown is the upper intersection of the plane containing the lumen axes the free surface of the epidural lumen which is diametrically opposed to the line of contact of the tubing.

The first condition assures that a catheter exiting the epidural lumen will be directed away from the direction of insertion of the needle, while the latter condition assures that the extension of the tip beyond the needle body will not make removal of the needle difficult by creating a barb which will make removal of the needle difficult.

A second piercing surface for the introducer lumen is cut angle delta with respect to the direction of insertion such that a second piercing surface intersects the line of contact at a second piercing point. When the method of the present invention is used to produce the improved tip of the present invention the two piercing points coincide forming a vertex. In this case it is preferred that the first piercing surface and the second piercing surface intersect at an angle theta of greater than about 40 Deg. Where theta is the sum of sigma and delta. This minimum of the angle theta assures that the vertex will have sufficient mass to assure its structural integrity and will not be subject to bending or fracture during insertion.

Since the epidural lumen is larger than the introducer lumen in the epidural-spinal needle, the limitation on the angle between the two piercing planes in combination with the limitation on the angle between the first piercing surface and the insertion direction of the needle assures that the opening through which a spinal needle exits the introducer lumen in the second piercing surface is closer to the vertex than the opening of the first piercing surface through which the catheter exits. This will assure that the spinal needle will be in the epidural space before it exits the introducer and will immediately encounter and penetrate the dura mater thereby avoiding impingement on hard tissue such as bone, cartilage or calcified ligaments which could bend or break a fine spinal needle.

It is further preferred that the introducer piercing surface is tangent to the line of contact at the vertex. This condition assures that integrity of the epidural tubing will be maintained throughout.

The limitations set forth above on the improved tip configuration of an epidural-spinal needle will slightly skew the direction of a spinal needle with respect to the direction of insertion. To limit the skewness of the path of the spinal needle it is further preferred that delta not be greater than about twice sigma. By so limiting the skewness, the friction between a spinal needle passing through the wall will be limited and the tactile sensing of tissue being pierced by a spinal needle passing through the introducer lumen will be maintained.

A divergence of the lumina in the unbonded region of the needle stock is obtained by bending the lumina. It is preferred that the divergence be obtained by bending the introducer lumen. Bending the introducer lumen while maintaining the epidural lumen straight assures that a force applied to the epidural needle tubing in the direction of insertion of the needle will not introduce bending moments in the epidural lumen.

A divergence of up to about 15 Deg. can readily be obtained by bending the introducer lumen without undue resistance to a spinal needle passing through the introducer or without loss of the tactile sensing of tissue being pierced by a spinal needle passing through the introducer lumen. If the introducer lumen is bent in a smooth curved path such as a circular arc then the divergence can be substantially increased. By using a circular arc and an angle of divergence of 25 to 30 Deg. the unbonded section of the needle can be reduced to less than 1.25 inches, thus making the epidural-spinal needle shorter, easier to use, and less costly to manufacture.

Support means are provided to enhance the structural rigidity of the diverging lumen. Preferably the means have a face plate having two passages passing there through. It is further preferred that the face plate has a first reference surface which is normal to the epidural lumen as it passes there through and a second reference surface which is normal to the introducer lumen as it passes there through.

The first reference surface has extensions which are symmetrically disposed about the epidural lumen and provide gripping surfaces which allow a force to be applied in the direction of insertion direction of the needle.

The second reference surface has tabs attached which are parallel to the direction of insertion of the epidural needle and extending toward the needle vertex and are preferably contoured to be gripped by finger and thumb.

A central support rib encases the diverging lumina and attaches to the faceplate providing additional support to the diverging lumina. This rib terminates at the other end with a stop which engages the epidural-spinal needle.

Preferably the face plate has extending therefrom hubs to allow for the attachment of one or more conventional syringes. These hubs can be made an integral part of the needle or alternatively part of the face plate.

In another preferred embodiment of the present invention the stock is color coded in such a manner that needles having different sizes and/or different point configurations can be readily distinguished.

BRIEF DESCRIPTION OF THE FIGURES

FIG. 7 also shows a spinal needle passing through the introducer lumen.

BEST MODE FOR CARRYING THE INVENTION INTO PRACTICE

In fabricating an epidural-spinal needle the appropriate gauge needle tubing should be selected based on its intended use. The epidural tubing should be chosen such that its lumen, the epidural lumen, passes the catheter for which it will be used. Generally the epidural lumen of the epidural-spinal needle should have a gauge size less than 14 gauge and preferably between approximately 16 and 20 gauge and preferably about 18 gauge.

When the epidural-spinal needle serves as an introducer for very small spinal needles of 25 to 32 gauge, the size of the smaller or introducer lumen tubing should be between 20 and 24 gauge. Such a gauge will accommodate a spinal needle of 25 to 32 gauge. The small spinal needle can in turn be used for a spinal puncture or microcatheters could be inserted intrathecally through the small gauge spinal needle.

Figure 1:
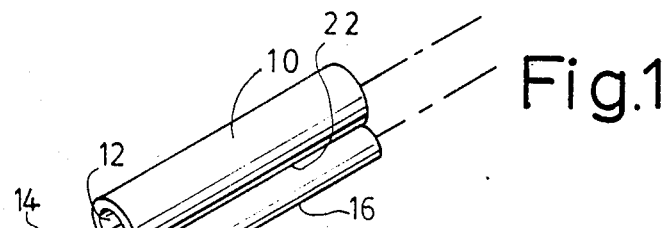
FIG. 1 illustrates the spacial relationship between a section of needle tubing having a lumen suitable for an epidural lumen and a section of needle tubing having a lumen suitable for introducer lumen.

FIG. 1 illustrates the spacial relationship segments of needle tubing having a lumen suitable for an epidural lumen and a section of needle tubing having a lumen suitable for introducer lumen. The larger gauge needle tubing is the epidural tubing 10 and has an epidural lumen 12. The epidural lumen 12 has an epidural lumen axis 14. The smaller needle tubing serves as introducer needle tubing 16 and has an introducer lumen 18 which has an introducer lumen axis 20. The epidural tubing 10 is placed in a side by side relationship with introducer tubing 16 such that their axes are parallel and a line of contact 22 between the tubing is established. The overall length of the tubing sections is a function of their intended use. Typically for needles intended to be used for adult patients this length will be between about 2.5 and 4.5 inches.

Figure 2:
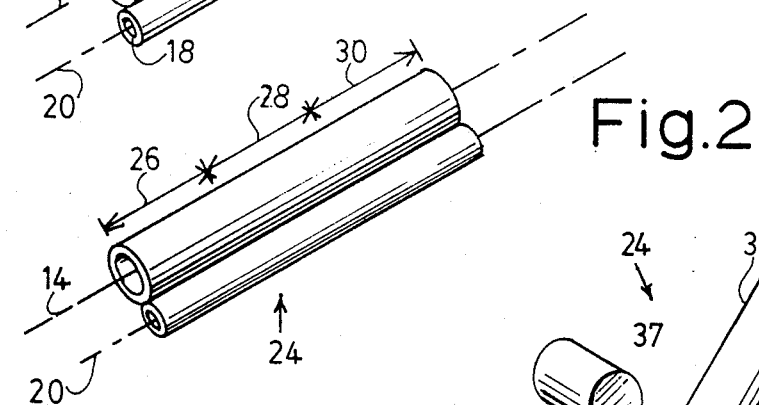
FIG. 2 shows a needle blank which is formed by bonding the tubing of FIG. 1.

The needle tubing segments are bonded along a segment of their line of contact 22 to form a needle blank 24 as is illustrated in FIG. 2. The bonded segment of the line of contact 22 starts at a first end which initiates the tip region 26 and continues along the line of contact 22 for a distance sufficient to form a tip region 26 and a needle body 28, leaving an unbonded region 30.

Welding is the preferred method of bonding the epidural tubing to the introducer tubing since welding provides a strong bond and the method can be easily automated. Electron beam welding or laser welding are preferred methods of welding since they can be focused to provide sharp temperature profiles and highly localized melting needed to bond the walls of the tubing without melting through the walls. Laser welding is further preferred if continuous tube stock is employed since laser welding is well suited to welding intermittent sections in continuous stock.

Figure 3:
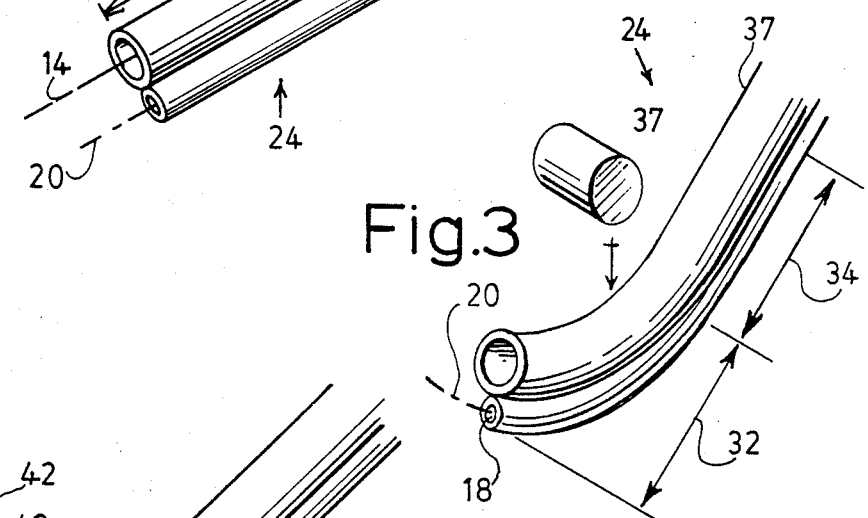
FIG. 3 shows the needle blank of FIG. 2 with the tip region being formed to provide an epidural tubing which will divert a catheter into the epidural space.

FIG. 3 shows the tip region 26 of the needle blank 24 of FIG. 2 being bent in the plane defined by the lumina axes (14, 20) to form a needle curved tip region 32 and leaving a straight needle body 34. It is preferred that the stylets not shown are positioned in the lumina during bending. Preferably the needle blank 24 is bent by employing a mandrel 36 to deform the crown 37 of the needle blank 24. The crown 37 is defined as the upper intersection of the plane defined by the lumen axes (14, 20) and the epidural lumen tubing 10, this intersection being diametrically opposed to the line of contact 22. The mandrel 36 having a diameter such that the minimum radius of curvature 38 of the epidural needle tubing 10 resulting from bending will preferably be between about $\frac{1}{2}$ and $\frac{5}{8}$ inches. When the tip is bent as shown, the epidural lumen axis after bending is convex with respect to the axis 20 of the introducer lumen 18 in the tip region 32 of the needle blank 24.

The direction of insertion 39 for the resulting needle is parallel to the line of contact 22 and the axes of the lumen in the needle body 34.

Figure 4:
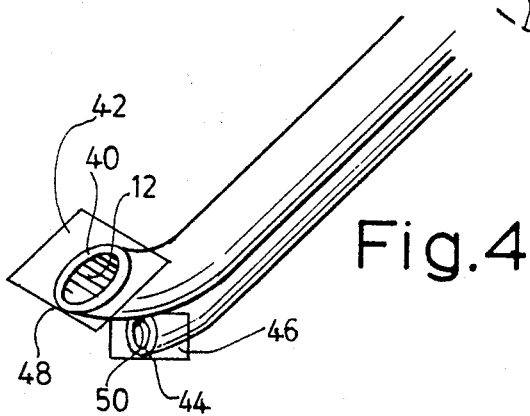
FIG. 4 illustrates the needle tip of FIG. 3 which has been cut forming piercing surfaces for the needle point.

After forming the tip region 32, piercing surfaces for the lumina are generated, preferably with stylets in the lumina. Referring to FIG. 4, a first piercing surface 40 for the epidural lumen 12 is generated by a cutting plane 42. A second piercing surface 44 is produced by a cutting plane 46.

The first piercing surface 40 intersects the line of contact 22 at a first piercing point 48 while the second piercing point 50 results from the second piercing surface 44 intersecting the line of contact 22. In general, the piercing points (48, 50) do not coincide. However it is preferred that the piercing points nearly coincide due to the restricted depth of the cross section of the epidural space. This depth is typically less than about 3 mm in lumbar spinal innerspaces. Having the piercing points (48, 50) coincide forming a joint point 50' as illustrated in FIG. 5 assures that the epidural lumen exit opening 51 and the introducer lumen exit opening 52 are in close proximity to the joint point 50'.

Figure 5:
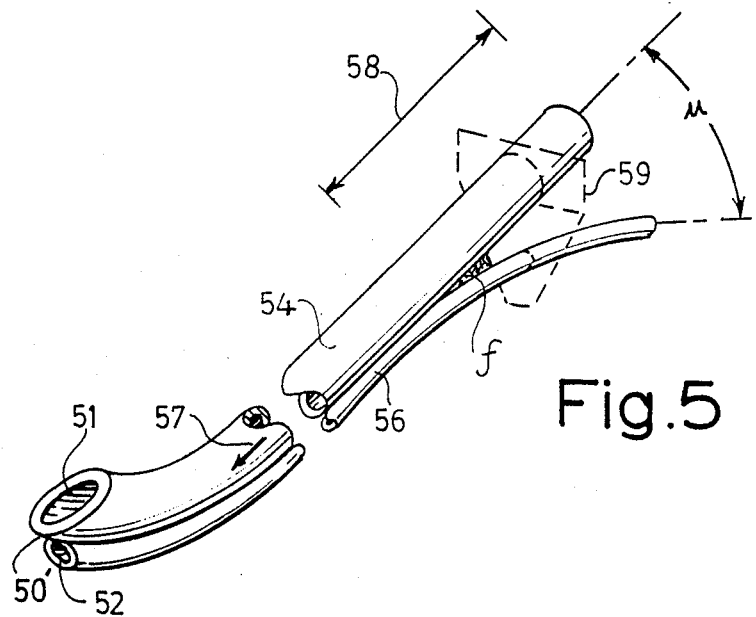
FIG. 5 shows a needle body terminating at one end with a needle point which is one embodiment of the improved point of the present invention. The other end has extensions of the epidural lumen and the introducer lumen which diverge which are stabilized by a faceplate and a fillet provided in the region where the two lumina meet.

In FIG. 5 the extensions of the epidural tubing 54 and the introducer tubing 56 diverge in the unbonded region 58. The divergence in the unbonded region 58 is introduced by bending the introducer tubing 56. It is preferred that the introducer tubing 56 be bent so that it diverges with respect to the epidural tubing 54. By maintaining the epidural tubing 54 straight a force applied to the epidural tubing 54 in the needle insertion direction 57 will not produce a bending moment about the epidural tubing 54. A divergence Mu of 15 Deg. can readily be obtained without loss of the tactile sensing of tissue being pierced by a spinal needle introduced through the introducer tubing 56. The divergence can be increased to about 30 Deg. when the curvature is gradually increased by a smooth curved path such as a circular path of radius R.

Means for assuring structural rigidity of the divergent lumina are attached to the diverging lumina (54, 56). Preferably the support means employs a face plate 59 having a first reference surface normal to the epidural lumen 54 and a second reference surface normal to the introducer lumen 56.

Figure 6:
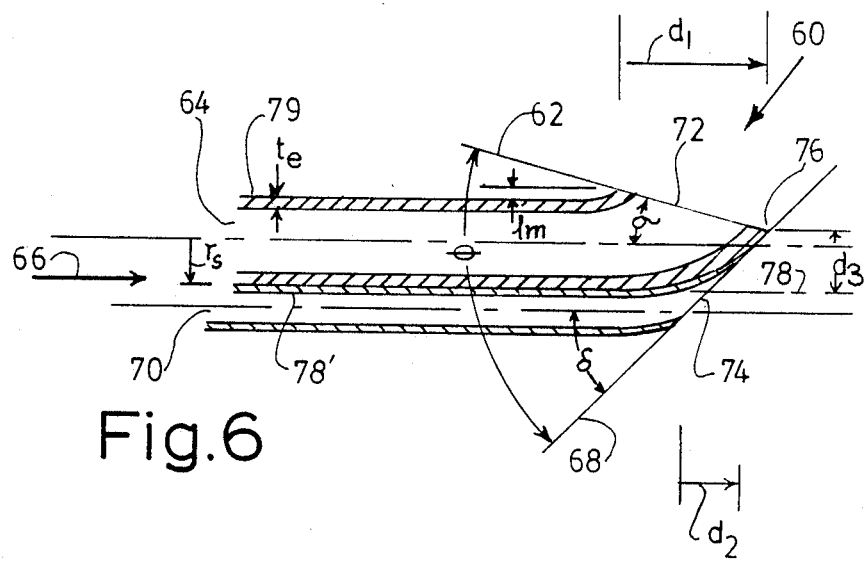
FIG. 6 illustrates a cross section of the improved point of FIG. 5. The phantom lines illustrate the continuation of the epidural and the introducer tubing before piercing surfaces are cut.

Details of the improved tip configuration for an epidural-spinal needle of the present invention are shown in FIG. 6. The tip 60 which is terminated by a first plane 62 which cuts the epidural lumen 64 at an angle sigma with respect to the direction of insertion 66 of the epidural-spinal needle. A second plane 68 cuts the introducer lumen 70 and makes an angle delta with respect to the insertion direction 66. The cutting planes generate an epidural piercing surface 72 and an introducer piercing surface 74 these piercing surfaces meeting at a vertex 76. Since the epidural lumen 64 is the larger of the two lumina, the introducer lumen 70 will terminate at a distance $d_2$ from the vertex 76 which is less than the distance $d_1$ at which the epidural lumen terminates from the vertex 76 when delta is equal to or greater than sigma.

Furthermore to assure that in the vicinity of the vertex 76 the needle point 60 has sufficient structural integrity to withstand the forces associated with insertion of the needle it is further preferred that the sum of sigma plus delta be greater than 40 Deg. An upper limit of this sum should be maintained below about 60 Deg. so as to facilitate the insertion of the needle.

To assure that the epidural lumen provides guidance to a catheter directing it into the epidural space the vertex 76 should be displaced a distance $d_3$ from the line 78 the extension of the line of contact 78' for the needle body, where $d_3$ is greater than the radius $r_s$ of the epidural tubing 79.

Furthermore to facilitate removal of the epidural spinal needle it is preferred that the first piercing surface 72 does not extend a distance $l_m$ beyond the crown 79 of the needle body by more than about four times the thickness $t_e$ of the epidural tubing.

Figure 7:
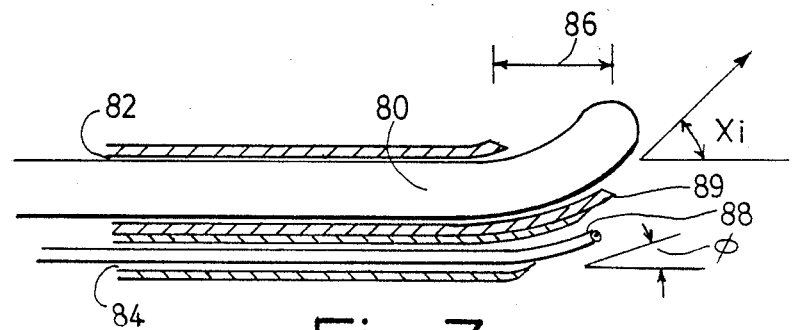
FIG. 7 shows a catheter inserted in the epidural lumen of FIG. 6 and exiting the tip.

FIG. 7 shows a catheter 80 positioned in the epidural lumen 82 and exiting from it with the angle Xi. This angle turns the catheter in such a direction that it will be directed along the epidural space assisted by the dural wall.

Since both the epidural lumen 82 and the introducer lumen 84 are bent in the tip region 86, a spinal needle 88 when exiting the introducer lumen 84 will be deflected in the direction of the catheter by an angle Phi. Maintaining delta not more than about approximately twice sigma will assure that the angle Phi will be substantially less than Xi. Having Phi substantially less than Xi provides two benefits. First, it assures that the spinal needle will enter the dural wall away from the area of the wall which might be effected by the vertex 89 of the tip. Second, it assures minimum resistance to the passage of the spinal needle 88 as it passes through the introducer lumen 84. By so limiting the resistance resulting from the passage of the spinal needle 84 as it passes through the tip, the divergence between the introducer lumen 84 and the epidural lumen 82 can be increased in the unbonded region of the needle to greater than 30 Deg. when bent in a smooth curve as illustrated in FIG. 5. without loss of the tactile response to tissue penetration by a spinal needle.

While Phi should be less than Xi having a non zero value of Phi is beneficial for spinal taps. Having Phi non zero results in a skewed puncture path which upon removal of the spinal needle assists in the sealing of the wall of the dura. Sealing the wall reduces the fluids that will transfer between the subarachoid and the epidural space and in turn reduces the likelihood of post dural headaches.

Figure 8:
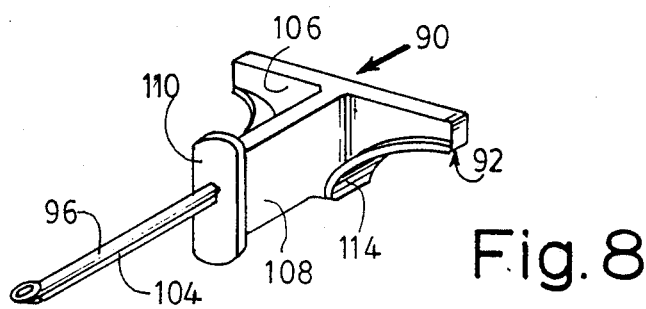
FIG. 8 is a prospective view of an epidural-spinal needle having a stock of a preferred embodiment of the present invention.
Figure 9:
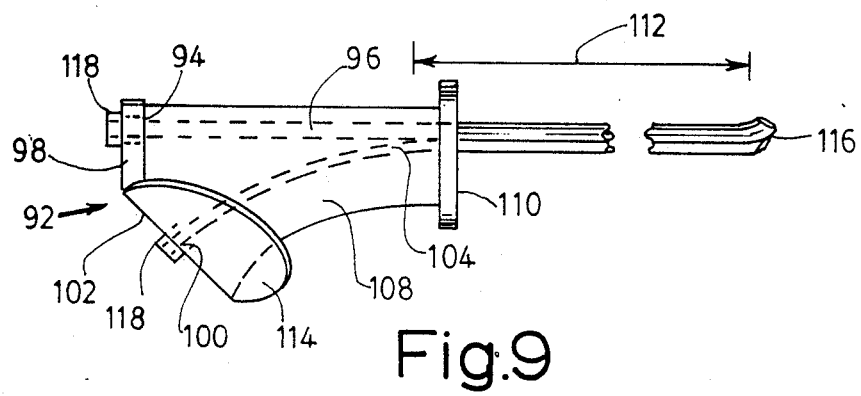
FIG. 9 is a side view of FIG. 8 showing the relationship of the diverging lumina to a two part face plate.

FIGS. 8 and 9 are a perspective view and a side view of an epidural-spinal needle of one embodiment of the stock of the present invention. The stock 90 is a preferred means for providing structural support for the diverging lumina to the unbonded region 58 shown in FIG. 5.

The stock 90 has a face plate 92 having a first passage 94 through which the epidural lumen 96 passes. Preferably a first reference surface 98 normal to the epidural lumen 96. A second passage 100 passes through the face plate 92 which preferably has a second reference surface 102 which is normal to the introducer lumen 104. Having the reference surfaces (98, 102) normal to their respective lumina (96, 102) provides surfaces which serve as a reference surface. These surfaces assist in aligning catheters and spinal needles for insertion and provide advantages in bonding the lumen to the reference surfaces.

The included angle between the two reference surfaces is equal to the divergence of the lumina at the reference surfaces since the reference surfaces are normal to their respective lumina. The face plate 92 is preferably provided with extensions 106 attached to the first reference surface and symmetrically disposed around the epidural lumen. The extensions provide gripping surfaces for inserting the epidural-spinal needle.

A stand alone faceplate 59 as shown in FIG. 5 can serve as a means for stabilizing the divergent lumina. However it is preferred to employ a fillet f at the joinder of the divergent lumina as illustrated in FIG. 5 in combination with the face plate 59. A central support rib 108 to encase the diverging lumina (96, 104) and attaches to the faceplate 92 is preferred to provide additional support to the diverging lumina (96, 104). A stop 110 attaches the support rib and engages the epidural-spinal needle body 112.

The second reference surface 102 preferably has tabs 114 attached extending toward the needle vertex 116 and are preferably contoured to be gripped by finger and thumb.

Preferably the faceplate has extending therefrom hubs 118 for the attachment of one or more conventional syringes. These hubs can be made an integral part of the needle or alternatively part of the face plate.

Figure 10:
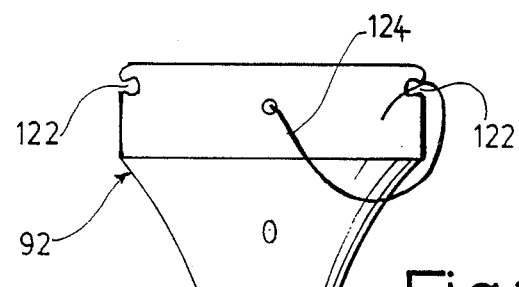
FIG. 10 is a schematic representation of a first means for holding a catheter at the face plate.
Figure 11:
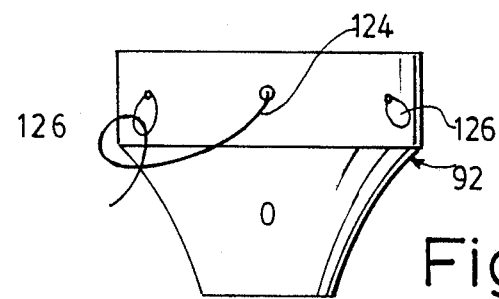
FIG. 11 is a schematic representation of a second means for holding a catheter at the face plate.
Figure 12:
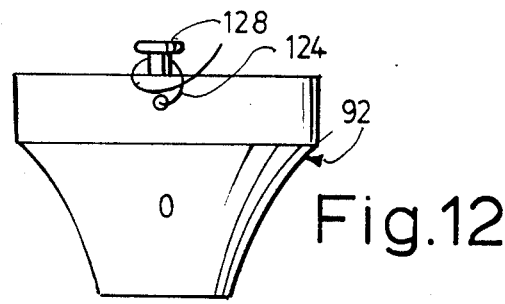
FIG. 12 is a schematic representation of a third means for holding a catheter at the face plate.

FIGS. 10, 11, and 12 illustrate various means for holding a catheter to a face plate 92 when a spinal needle is being inserted. FIG. 10 illustrates notches in the face plate 122 into which a catheter 124 can be placed. FIG. 11 illustrates loops 126 for holding the catheter 124. While FIG. 12 shows the catheter being held by a knob and hook 128.

What I claim is:

1. An improved epidural-spinal needle having an epidural lumen bounded by epidural tubing which is larger than and joined along a line of contact to introducer tubing bounding an introducer lumen, the tubes forming a straight needle body having a direction of insertion parallel to the lumen axes, the improvement comprising:
   a tip region where the lumen axes are curved in the plane defined by the lumen axes, the epidural lumen being convex with respect to the introducer lumen;
   a first piercing surface terminating the epidural lumen, said first piercing surface being inclined with respect to the direction of insertion by an angle sigma and intersecting the line of contact at a first piercing point; and
   a second piercing surface terminating the introducer lumen being inclined with respect to the direction of insertion by an angle delta and intersecting the line of contact at a second piercing point, said first piercing point and said second piercing point being nearly coincident and forming a vertex.

2. The improved needle of claim 1 wherein said axes are curved such that the minimum radius of curvature of the needle tip is between about ½ and ⅝ inches, sigma is less than 30 Deg. and said vertex is located at a distance from a line defined by the line of contact of the needle body which is greater or equal to the radius of the epidural tube.

3. The improved needle of claim 2 wherein sigma is less than about 30 Deg. and sigma plus delta is greater than about 40 Deg. and less than 60 Deg.

4. The improved needle of claim 3 wherein delta is not greater than about twice sigma.

5. The improved needle of claim 4 wherein said first piercing surface extends beyond the needle body by not more than four times the thickness of the wall of said epidural tubing.

6. The improved needle of claim 5 wherein said second piercing surface is tangent to said line of contact at said vertex.

7. An improved needle stock for a epidural-spinal needle having a bonded region where an epidural lumen and an introducer lumen are bonded and an unbonded region where the lumina diverge, the improvement comprising:
   a face plate having first reference surface with a first passage there through and a second reference surface with a second passage there through, said second reference surface being inclined with respect to the first reference surface such that the epidural lumen will pass through said first reference surface substantially normal to said first reference surface and the introducer lumen will pass through said second reference surface substantially normal to said second reference surface.

8. The needle stock of claim 7 further comprising:
   a central support rib attached to face plate and which provides for encasement of the diverging lumina.

9. The needle stock of claim 8 further comprising:
   a stop engaging the bonded region of the needle and attached to the support rib.

10. The needle stock of claim 9 further comprising:
    extensions providing gripping surfaces attached to said first reference surface and symmetrically disposed about the epidural lumen; and
    tabs attached to said second reference surface of the stock.

11. The needle stock of claim 10 further comprising:
    means for holding a catheter to said face plate, said means for holding a catheter to said face plate being attached to said face plate.

12. The needle stock of claim 10 wherein said tabs attached to said second reference surface are contoured to be gripped by a finger and thumb.

13. The needle stock of claim 7 further comprising:
    a fillet spaced apart from said face plate for engaging the epidural tubing and the introducer tubing where divergence of the lumen begins.

14. The needle stock of claim 13 further comprising:
    means for holding a catheter to said face plate, said means for holding a catheter to said face plate being attached to said face plate.

15. A method for manufacturing a epidural-spinal needle comprising the steps of:

aligning epidural tubing having an epidural lumen with introducer tubing having an introducer lumen in a side by side relationship so as to form a line of contact between said first epidural tubing and said introducer tubing;

bonding along the line of contact for a distance sufficient to form a needle blank having a tip end, a needle body, and an unbonded region, said line of contact in said needle body defining the needle insertion direction;

bending said tip region of said needle blank in the plane defined by the axes of said lumen such that after bending said epidural lumen is convex with respect to said introducer lumen;

cutting a first piercing surface intersecting the epidural tubing inclined by an angle sigma to said insertion direction where sigma is less than 30 Deg.; and cutting a second piercing surface intersection the introducer tubing inclined to said insertion direction by an angle delta.

16. The method of claim 15 wherein said first piercing surface terminates in a first piercing point and said second piercing surface terminates in a second piercing point, said first piercing point and said second piercing point are nearly coincident, and the sum of sigma plus delta is greater than 40 Deg. and less than 60 Deg.

17. The method of claim 16 further comprising the steps of:

bending the tubing of the unbonded segment so as to provide a divergence of at least 10 Deg. in the unbonded tubing;

engaging said diverging tube segments with a faceplate; and attaching hubs to said diverging tube segments 18. The method of claim 17 wherein said method of bonding is selected from the group of electron beam welding and laser welding, and further wherein the method of cutting is selected from the methods of electrodeposition cutting and electrochemical grinding.

* * * * *